United States Patent [19]

Masuda et al.

[11] Patent Number: 4,692,529

[45] Date of Patent: Sep. 8, 1987

[54] METHOD FOR SYNTHESIZING A MAGENTA COUPLER BY SELECTIVELY ETHERIFYING 4-HYDROXY-5-PYRAZOLONE

[75] Inventors: Kasaku Masuda, Akishima; Ryosuke Sato; Fumio Ishii, both of Hino; Kazuhiko Kimura; Hidetaka Ninomiya, both of Hachioji, all of Japan

[73] Assignee: Konishiroku Photo Industry Co., Ltd., Tokyo, Japan

[21] Appl. No.: 550,510

[22] Filed: Nov. 10, 1983

Related U.S. Application Data

[63] Continuation of Ser. No. 312,317, Oct. 16, 1981, abandoned.

[30] Foreign Application Priority Data

Oct. 17, 1980 [JP] Japan .................................. 55-146074

[51] Int. Cl.$^4$ .................... C07D 231/28; C07D 401/12
[52] U.S. Cl. ...................................... 546/141; 546/279;
548/162; 548/18 D; 548/195; 548/221;
548/251; 548/255; 548/261; 548/263; 548/327;
548/336; 548/364; 548/365
[58] Field of Search ................ 548/365, 364, 195, 162,
548/336, 327, 261, 180, 251, 221, 263, 255;
546/141, 279

[56] References Cited

U.S. PATENT DOCUMENTS 3,419,391 12/1968 Young .................................. 548/365

FOREIGN PATENT DOCUMENTS 33121 10/1963 Finland .

OTHER PUBLICATIONS

Greene, Protective Groups in Organic Synthesis, Wiley, N.Y., 1981, pp. 148-149, 267-269.

*Primary Examiner*—Henry R. Jiles
*Assistant Examiner*—Kurt G. Briscoe
*Attorney, Agent, or Firm*—Finnegan, Henderson, Farabow, Garrett & Dunner

[57] ABSTRACT

A method for synthesizing a magenta coupler. The synthesis is carried out through (1) 3-pyrazoline-5-ones which are obtained by substituting a blocking group at the nitrogen atom in the second position thereof; or (2) pyrazoles which are obtained by substituting a blocking group at the hydroxyl group bonded in the fifth position thereof. The magenta coupler obtained has the formula

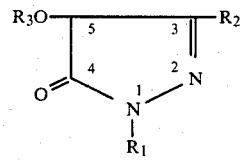

Formula [I]

wherein $R_1$ is an aryl or heterocyclic group, $R_2$ is an acylamide, anilino or ureido group, and $R_3$ is an alkyl, aryl, or heterocyclic group.

6 Claims, No Drawings

METHOD FOR SYNTHESIZING A MAGENTA COUPLER BY SELECTIVELY ETHERIFYING 4-HYDROXY-5-PYRAZOLONE

This application is a continuation of application Ser. No. 312,317, filed 10/16/81, now abandoned.

The present invention relates to a method for synthesizing a magenta coupler.

In general, since silver halide photographic light-sensitive materials have high sensitivities and excellent image qualities, they have been utilized for various photographic uses. However, since silver halide photographic light-sensitive materials require a large amount of silver, the recent shortage of silver and the resultant instability of material costs have created a demand for economizing the amount of silver used.

To meet this demand, silver economizing type silver halide photographic light-sensitive materials have been sought, and some have already been proposed. For example, Japanese Patent Examined Publication No. 13576/1974 discloses the so-called two equivalent coupler which is constituted to need only two silver atoms, whereas the conventional coupler requires four silver atoms to form one molecular dye, by introducing a substituent to the active site of a color former. This method is theoretically capable of reducing the amount of silver used to one half of that needed for the so-called four equivalent coupler. However, since in practice the two-equivalent coupler has higher efficiency in use of silver than the four-equivalent coupler the amount of silver required can be reduced to less than one half. Therefore, in recent years two-equivalent type couplers have generally been used.

Meanwhile, whether two-equivalent couplers or four-equivalent couplers are used, a method exists for processing a silver halide photographic light-sensitive material containing color couplers, after being imagewise exposed, in a color developing solution containing an aromatic primary amine developing agent thereby to form a dye image. Of the color couplers used, the yellow color coupler generally has an active methylene group which is useful for forming yellow dye by coupling with the oxidized product of an aromatic primary amine developing agent. Practically useful yellow couplers include α-acyl acetanilide couplers. Moreover, pyrazolone couplers are generally known as magenta couplers and phenol or naphthol couplers are well known as cyan couplers.

The two-equivalent coupler has a structure wherein one of the hydrogen atoms at the active site of the coupler, i.e., the position in which a coupling reaction takes place with the oxidized product of the aromatic primary amine developing agent contained in a color developing solution, is substituted with a radical removable at the time of the coupling reaction. The two-equivalent couplers are advantageously highly efficient in the use of silver and also adaptable to rapid processing. Accordingly, α-acyl acetanilide yellow couplers and phenol or naphtol cyan couplers have been used in practice.

However, the art has heretofore not known a highly efficient synthesis for pyrazolone magenta couplers; accordingly, they have not been a practical reality. Regarding two-equivalent pyrazolone magenta couplers, U.S. Pat. No. 3,419,391 and Japanese Patent Publication Open to Public Inspection (hereinafter referred to as Japanese Patent O.P.I. Publication) Nos. 112343/1976 and 90932/1977 describe compounds wherein a substitution is made to the oxygen in the fourth position of the pyrazolone ring and also disclose coupler synthetic methods including the reaction of 4,5-dihydroxy pyrazole with halogenated alkyl or halogenated aryl. These methods, however, are hardly considered realistic because of their extremely low yields.

It is, therefore, an object of the present invention to provide a method for synthesizing in high yield a two-equivalent pyrazolone magenta coupler. It has been discovered that the above object is attainable by a method for the synthesis of a magenta coupler comprising the synthesis carried out through (1) 3-pyrazoline-5-ones which are obtained by substituting a blocking group at the nitrogen atom in the second position thereof; or (2) pyrazoles which are obtained by substituting a blocking group at the hydroxyl group bonded in the fifth position thereof. The magenta coupler obtained has the formula:

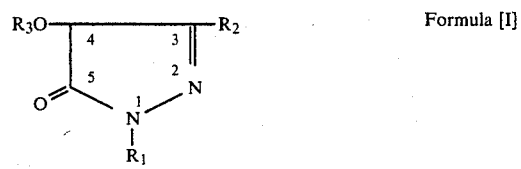

Formula [I]

wherein $R_1$ represents aryl or heterocyclic group; $R_2$ represents an acylamide, anilino or ureido group; and $R_3$ represents alkyl, aryl or heterocyclic group.

This method for synthesizing the magenta couplers of the present invention is illustrated in detail below.

The $R_1$, $R_2$ and $R_3$ substituents of the two-equivalent pyrazolone magenta coupler represented by the Formula [I] include, besides the foregoing groups, the groups described in U.S. Pat. No. 3,419,391 and Japanese Patent O.P.I. Publication Nos. 112343/1976 corresponding to Great Britain Patent No. 1,535,567 and No. 90932/1977 corresponding to U.S. Pat. No. 4,146,396, the disclosures of which are specifically incorporated by reference herein.

Specifically, $R_1$ represents such aryl groups as phenyl, napthyl, 2-chlorophenyl, 2,6-dichlorophenyl, 2,4,6-trichlorophenyl, 3,5-dibromophenyl, 3-nitrophenyl, 4-(2,4-di-t-amyl phenoxy)acetamidophenyl, pentafluorophenyl, 4-phenoxyphenyl, 2,6-dimethyl-4-methoxyphenyl, 3-(N,N-diethyl sulfamyl)phenyl, 2,6-dichloro-4-methoxyphenyl, 2-chloro-4,6-dimethyl phenyl, pentachlorophenyl, 2,6-dichloro-4-carboxyphenyl, 2,5-dimethoxy-3,4-dichlorophenyl, 4{α-(3-pentadecyl phenoxy)butylamide}phenyl and the like; and such heterocyclic groups as 2-thiazolyl, 2-benzothiazolyl, 2-benzoxazolyl, 2-imidazolyl, 2-benzoimidazolyl and the like.

$R_2$ represents such acylamide groups as α-(3-pentadecyl phenoxy)butylamide, n-tetradecane amide, α-(2,4-di-t-amyl phenoxy) butylamide, 3-[α-2,4-di-t-amyl phenoxy)butylamide]benzoamide, 3-acetylamide benzamide and the like; such anilino groups as phenylamino, O-chlorophenylamino, 2,4-dichlorophenylamino, 2-chlor-5-tetradecane amidoanilino, 2,4-dichlor-5-hexadecyl oxyanilino, 2-chlor-5-octadecenyl succineimidoanilino, 2-chlor-5-[α-{(3-t-butyl-4-hydroxy)phenoxy}tetradecane amide]anilino, 2-chlor-3-[2-{1,3-(1-hexadecyl-5-trichloromethyl)}benzimidazolyl-]anilino, 2-methoxy-5-(4-hexadecyl oxybenzamide)anilino and the like; and such ureido groups as phenyl ureido, 3-{α-(2,4-di-t-amyl phenoxy) butylamide}phenyl ureido and the like.

$R_3$ represents such alkyl groups as n-butyl, hexyl, dodecyl, and the like; such substituted alkyl groups as ethoxycarbonyl ethyl, methoxyethyl aminocarbonyl propyl, phenyl methyl, ethoxyethyl, 2-cyclopentanoneyl, methylsulfonyl butyl, tolyl sulfonyl methyl, 1-benztriazolyl methyl, 2-benzothiazolyl ethyl, 3-carboxypropyl, perfluoropropyl and the like; such aryl groups as phenyl, 4-nitrophenyl, 3-cyanophenyl, 4-methyl sulfonyl phenyl, 4-hydroxyphenyl and the like; and such heterocyclic groups as 2-pyranyl, 2-pyridyl, 3-isoquinolyl, 1-phenyl tetrazolyl, 2-benzoxazolyl, triazolyl, 3-indolyl and the like.

4-hydroxy-3-pyrazoline-5-ones which are substituted at the nitrogen atom in the second position by a blocking group are preferably represented by the Formula [III] below. 4-hydroxypyrazoles which are substituted at the hydroxyl group bonded in the fifth position by a blocking group may preferably be represented by the Formula [II] below.

In addition, the words "blocking group" in this invention mean the protective groups described in Japanese Patent O.P.I. Publication No. 53330/1980 corresponding to U.S. Pat. No. 4,310,612, the disclosure of which is specifically incorporated by reference herein.

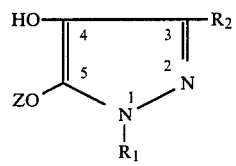

Formua [II]

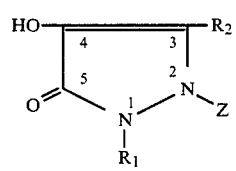

Formula [III]

wherein $R_1$ and $R_2$ each represents the same group as shown in Formula [I]; and Z represents a blocking group preferably having the following Formulas [IV], [V] and [VI]:

Formula [IV]

wherein X is oxygen or sulfur; $R_4$ is selected from the group consisting of hydrogen, an alkyl, aryl, heterocyclic, alkoxy, aryloxy, heterocyclic oxy, amino, alkylthio, arylthio and heterocyclic thio.

Specific blocking groups represented by Formula [IV] include formyl, acetyl, benzoyl, pivaloyl, furanoyl, carbamoyl, dimethyl carbamoyl, phenyl carbamoyl, 1-piperidino-carbamoyl, 1-pyrrolidinocarbamoyl, methoxycarbonyl, phenyl thiocarbonyl, chloroacetyl, ethoxythiocarbonyl, benzil-xanthogenyl and the like.

Formula [V]

wherein $R_5$ is selected from the group consisting of alkyl, aryl, heterocyclic, hydroxy, and amino.

Specific blocking groups represented by Formula [V] include methyl sulfonyl, phenyl sulfonyl, methyl aminosulfonyl and the like.

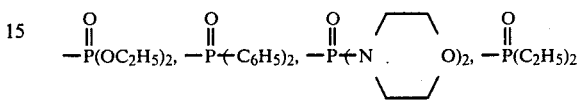

Formula [VI]

wherein $R_6$ is selected from the group consisting of alkyl, silyl, and phosphoryl.

Specific blocking groups represented by Formula [VI] include methyl, isopropyl, t-butyl, benzyl, methoxymethyl, 2-pyranyl, phenacyl, trialkyl silyl, triaryl silyl, trimethyl silyl, diethyl methyl silyl, triphenyl silyl,

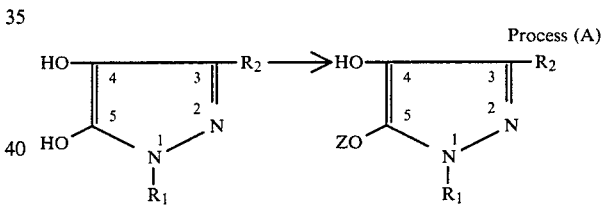

and the like.

As blocking groups other than these described above, there may also be used protective groups disclosed in, for example, "Protective Groups in Organic Chemistry" published in 1973 by Plenum Press and "Compendium of Organic Synthetic Methods" written by Jan T. Harrison et al. and published in 1971 and 1974 by Wiley &. Sons, the disclosures of which are specifically incorporated by reference herein, and the like.

The outline of the methods for obtaining compounds having Formulas [II] and [III] follow. Firstly, Process (A), wherein a blocking group is introduced to the hydroxyl group bonded in the fifth position of 4-hydroxy-2-pyrazoline-5-ones, can be diagrammed as follows:

Process (A)

In the conventional method for the synthesis of two-equivalent pyrazolone magenta couplers, the etherification by the two-equivalent coupler substituent to the hydroxyl group bonded in the fourth position of 4-hydroxy-2-pyrazoline-5-one requires a vigorous reaction. Probably because of this, the compound itself decomposes, thus leading to extremely low yields of two-equivalent couplers. It has been discovered, however, that the introduction of a blocking group to the hydroxyl group bonded in the fifth position, prior to the above-mentioned etherification reaction, enables one to obtain a satisfactory yield of the blocking group-substituted compound.

This shows that with respect to the blocking reaction, the hydroxyl group bonded in the fifth position of 4-hydroxy-2-pyrazoline-5-one has higher reactivity than that bonded in the fourth position. Accordingly, a highly efficient synthesis of two-equivalent pyrazolone magenta couplers has been discovered by the application of the blocking reaction to intermediates in accordance with the above-described discovery.

Regarding such synthetic methods, the description of the application of blocking reactions as examples of the synthesis of cyan couplers is found in Japanese Patent O.P.I. Publication No. 123341/1975, but such methods of applying blocking reactions, as is described also in Japanese Patent O.P.I. Publication No. 117422/1975, is not necessarily applicable to all the coupler compounds. In the case of the compounds described in the above-mentioned Publications as well as in Japanese Patent O.P.I. Publications No. 26038/1976 and No. 26039/1976, these Publications describe the direct substitution of two-equivalent substituents through oxygen atoms without introducing any blocking groups.

Blocking groups applied to Process (A) are generally used in the form of such blocking agents as halides, acid anhydrides, active olefins, esters and the like thereof, and their synthesis with blocking reactions may take place in the presence of such a catalyst as an inorganic base, e.g., sodium hydroxide, potassium carbonate and the like, an organic base, e.g., pyridine, triethyl amine and the like, and an acid, e.g., sulfuric acid, methane sulfonic acid, aluminum chloride, boron trifluoride and the like, or with no catalyst, but when no catalyst is used in the synthesis, reactions may be carried out in a solvent that is usable in an ordinary method of synthesis.

Subsequently, Process (B) for the introduction of blocking groups to the nitrogen atom in the second position of 4-hydroxy-2-pyrazoline-5-ones may be expressed as shown below:

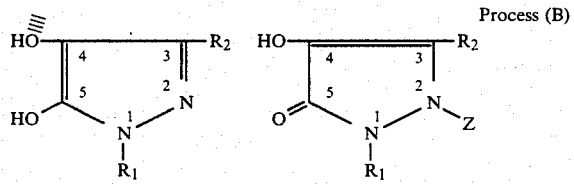

Process (B)

In accordance with the present invention, compounds having Formula [I] may be synthesized in high yields also from compounds obtained by introducing blocking groups to the nitrogen atom in the second position of 4-hydroxy-2-pyrazoline-5-ones.

Blocking groups usable in Process (B), similarly to Process (A), are used in the form of blocking agents such as halides, acid anhydrides, active olefins, esters and the like thereof, and the synthesis with blocking reactions may take place in the presence of such a catalyst as aluminum chloride, boron trifluoride and the like, whereby 4-hydroxy-3-pyrazoline-5-ones having a blocking group in the second position thereof may be synthesized.

The above blocking reaction to the nitrogen atom in the second position of 4-hydroxy-2-pyrazoline-5-ones can be achieved only when carried out in accordance with the present invention which utilizes the fact that the nitrogen atom in the second position has a higher reactivity than the hydroxyl group bonded in the fifth position depending on the kind or reaction condition of the substituents in the first and third positions of 4-hydroxy-2-pyrazoline-5-ones.

Regarding the difference in the reactivity of 4-hydroxy-2-pyrazoline-5-ones according to the kind or reaction condition of the above substituents, a report by R. E. Bowman et al. described in p. 1583 of "Journal of Chemical Society" published in 1957 tells that in the case where the substituent in the third position is ethoxy carbonyl group, the blocking reaction takes place on the nitrogen atom in the second position, while Japanese Patent O.P.I. Publication Nos. 147320/1976 corresponding to U.S. Pat. No. 4,062,683 and 31738/1977 corresponding to U.S. Pat. No. 4,061,498 describes that as for 4-substituent-2-pyrazoline-5-ones, even when the substituent in the third position is the same, if the reaction condition differs, the blocking reactivity would differ accordingly. The disclosure of these publications are specifically incorporated by reference herein.

In brief, the method for the synthesis of magenta couplers of the present invention is characterized by carrying out the synthesis of magenta coupler compounds having Formula [I] by utilizing skillfully the reactivity that has been unknown relating to Process (A) or (B) for obtaining compounds having Formula [II] or [III], which are the materials efficient for synthesizing the magenta couplers of the present invention.

In the production method of the present invention, it is desirable also to include in the foregoing Process (A) and (B) such a roundabout way that at the time of introducing a blocking group to the nitrogen atom in the second position or to the hydroxyl atom in the fifth position of 4-hydroxy-2-pyrazoline-5-ones, a substitution of the hydroxyl group bonded in the fourth position in temporarily made by acyl group and the like which is more subject to deblocking than the forgoing group, and further to this the blocking group is then introduced to substitute the nitrogen atom in the second position or to the hydroxy atom in the fifth position, and afterward, the acyl group subject to deblocking and which was introduced to the hydroxyl group bonded in the fourth position is deblocked.

To achieve the object of the present invention, compounds having Formula [II] are preferred to those having Formula [III], and blocking groups having Formula [IV] are preferred.

The outline of the method for the etherification of the hydroxyl group bonded in the fourth position of compounds having Formulas [II] and [III] by two-equivalent substituents is then illustrated with reference to Process (C) below:

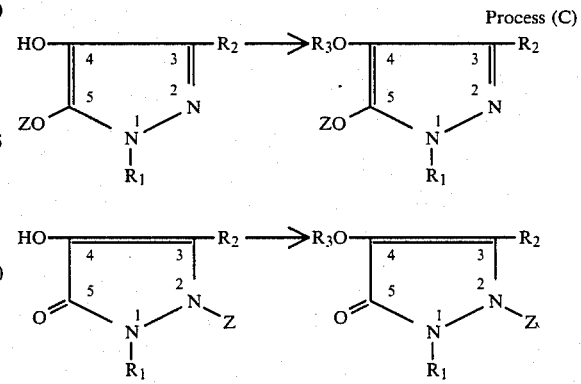

Process (C)

The method of the synthesis for the alkyl-etherification, aryl-etherification or heterocyclic-etherification of the hyroxyl group bonded in the fourth position of both the above compounds in Process (C) may be carried out using alkyl-etherification agents, aryl-etherification agents or heterocyclic-etherification agents in such normal manners as described in, e.g., "Survey of Organic Synthesis" written by C. A. Buehler et al., published in 1970 by John Wiley & Sons, the disclosure of which is specifically incorporated by reference herein. Examples of such etherification reactions include a method for the reaction with halides in the presence of a basic catalyst, a method for the dehydration-condensation with hydroxides and a method for the addition to active olefins or epoxides.

Finally, the method for the dissociation or removal of blocking groups from both the etherified compounds obtained by Process (C) shown above is briefed with reference to Process (C) below:

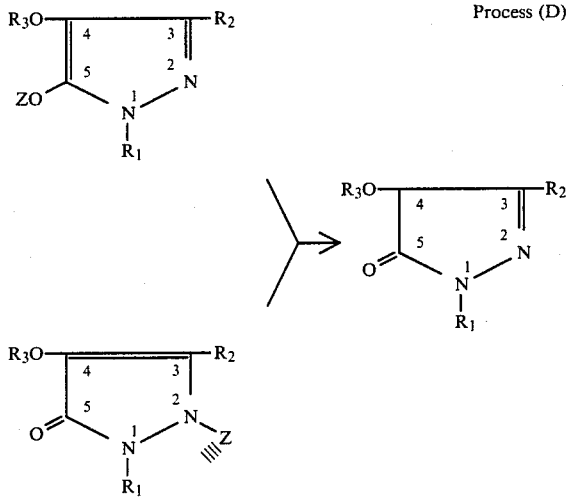

Process (D)

Dissociation or removal of the above blocking group from pyrazoline-5-one compounds having the blocking group introduced to the nitrogen atom in the second position or to the hydroxyl group bonded in the fifth position may be effected usually by utilizing hydrolysis, solvolysis, oxidation, reduction, elimination or a photolysis reaction. Various examples of these reactions are described in the aforementioned literatures "Protective Groups in Organic Chemistry" and "Compendium of Organic Synthetic Methods."

The synthetic method of the present invention is illustrated in detail with reference to the examples below, but the present invention is not limited thereto:

EXAMPLE 1

Synthesis of 1-(2,4,6-trichlorophenyl)-3-{3-[α-(2,4-di-t-amyl phenoxy) acetamide]benzamide}-4-(4-nitrophenoxy)-5-pyrazolone (coupler (3) described in U.S. Pat. No. 3,419,391).

Process (A): Substitution of blocking group

Ten grams of 1-(2,4,6-trichlorophenyl)-3-{3-[α-(2,4-di-t-amyl phenoxy) acetamide]benzamide}-4-hydroxy-5-pyrazolone are dissolved in 100 ml of pyridine. To the solution are added at room temperature with stirring 1.7 g of N,N-dimethyl carbamoyl chloride to be reacted for a period of two hours. The resulting reaction product is poured into 350 ml of iced water, and extracted with the use of 100 ml of ethyl acetate. The solvent is removed by distillation and the residuum is recrystallized by methanol, thus yielding 9.9 g (90%) of colorless prism crystals having a melting point of 125°–128° C. (dec).

Process (C): Etherification by two-equivalent substituent

Process (D): Dissociation or removal of blocking group 9.9 g of 1-(2,4,6-trichlorophenyl)-3-}3-[α-(2,4-di-t-amyl phenoxy)acetamide]benzamide}-4-hydroxy-5-dimethyl carbamoyl oxypyrazole are dissolved in 100 ml of DMF, and 2 g of KOH are also completely dissolved in the solution.

2.4 g of p-nitrobenzene are subsequently added to the resulting solution and stirred at room temperature over a period of 20 hours. To the reaction liquid are added 50 ml of water, and the reaction of the liquid is effected for a period of 30 minutes by heating to 50° C. The resulting reaction liquid is poured into 350 ml of iced water, neutralized by acetic acid, and extracted by ethyl acetate. The solvent is removed by distillation, and the residuum is recrystallized from a mixture of chloroform with n-hexane, thereby yielding 7.3 g (70%) of a colorless powder having a melting point of 206.5°–207° C.

The thus-obtained product was confirmed to be identical with the coupler (yield: 0.3%) synthesized in accordance with the method described in the foregoing U.S. Patent publication as a result of being subjected to a mixed melting point test and comparison test with an infrared spectrometer.

In addition, in the case of being synthesized in accordance with the description in the U.S. Patent, what was obtained in a small amount aside from the objective product was nothing but the intermediate (3) described in the U.S. Patent, and all the rest was a resin-like decomposed product.

Alternative Method for the Synthesis of the above Coupler

Process (B): Substitution of blocking group

Ten grams of 1-(2,4,6-trichlorophenyl)-3-{3-[α-(2,4-di-t-amyl phenoxy)acetamide]benzamide}-4-hydroxy-5-pyrazolone are dissolved in 100 ml of methylene chloride and to the solution are added 2.6 g of anhydrous aluminum chloride. To this, while maintaining the temperature at 0°–5° C., are added 2 ml of pyridine. While the temperature is maintained, 1.7 g of ethyl chloroformate are added over one hour; further, 4 ml of pyridine are slowly added. The reaction of the resulting mixture takes place for three hours. The resulting reaction liquid is poured into an aqueous 1N HCl solution to sufficiently wash the methylene chloride stratum. The solvent is removed by distillation under reduced pressure, and to the resulting residuum are added 100 ml of acetonitrile thereby to produce 3 g of light yellow amorphous crystals having a melting point of 96°–108° C.

Process (C): Etherification by two-equivalent substituent

Process (D): Dissociation or removal of blocking group

A coupler was obtained by Processes (C) and (D) similar to the foregoing processes, using 1-(2,4,6-trichlorophenyl)-2-ethoxy carbonyl-4-hydroxy-3-{3-[α-(2,4,-di-t-amyl phenoxy)acetamide]benzamide}-3-pyrazoline-5-one. Total yield: 15%. Melting point: 205°–206.5° C.

The resulting product was confirmed to be identical with the couplers obtained by the foregoing Processes (A), (C) and (D), as a result of being subjected to a mixed melting point test and comparison test by an infrared spectrometer.

In Process (B), when 4-acetoxypyrazolone was used in place of the 4-hydroxy pyrazolone, the acetoxy group in the fourth position is hydrolysed during the process, whereby the objective product was obtained in higher yield. Total yield: 30%.

EXAMPLE 2

Synthesis of 1-(2,4,6-trichlorophenyl)-3-{2-chloro-5-[α-(2,4-di-t-amyl phenoxy)-butylamide]anilino}-4-(4-nitrophenoxy carbonyl methoxy)-5-pyrazolone (the exemplified coupler (12) described in Japanese Patent O.P.I. Publication No. 112343/1976).

Ten grams of 1-(2,4,6-trichlorophenyl)-3-{2-chlor-5-[α-(2,4,-di-t-amyl phenoxy)butylamide]anilino}-4-hydroxy-5-pyrazolone are dissolved in 100 ml of dimethyl sulfoxide, and to the mixture are added 2 g of benzyl chloride and 3 g of potassium carbonate to effect the reaction thereof over eight hours in a nitrogen atmosphere at room temperature. The resulting reaction liquid is poured into iced water and extracted by use of ether.

The principal product was confirmed to be identical with the coupler (yield: 0.2%) synthesized in accordance with the description in the aforesaid Japanese Patent O.P.I. Publication as a result of being subjected to a mixed melting point test and comparison test with an infrared spectrometer.

EXAMPLE 3

Synthesis of 1-(2,4,6-trichlorophenyl)-3-{3-[α-2,4-di-t-amyl phenoxy)acetamide]benzamide}-4-benzyloxy-5-pyrazolone Process (A): Substitution of blocking group Ten grams of 1-(2,4,6-trichlorophenyl)-3-{3-[α-2,4,-di-t-amyl phenoxy)acetamide]benzamide}-4-hydroxy-5-pyrazolone are dissolved in a mixture of 100 ml of ethyl acetate with 100 ml of acetonitrile. To the solution are added 1.5 g of pyridine. After that, 2 g of methane chloride are added over an hour. After 20 hours of reaction, the reaction product is poured into 500 ml of iced water and extracted by the addition of ethyl acetate.

The solvent is removed by distillation, and the resulting residuum is crystallized by ethyl acetate/n-hexane, thus yielding 9 g (80%) of light yellow needle crystals having a melting point of 129°-130° C.

Field Desorption Mass Spectrometry by electroytic elimination: M+ 764.

Process (C): Etherification by two-equivalent substituent

Process (D): Dissociation of blocking group 9 g of the resulting crystals are dissolved in 100 ml of dimethyl sulfoxide and to the mixture are added 2 g of NaOH. The solvent is concentrated under reduced pressure, and the thus-obtained product is refined by separation in the manner of silica gel column chromatography, thereby yielding 1 g of a yellow caramel-like product. This was confirmed to be the objective product as a result of being subjected to a mass spectrometry test. A nuclear magnetic resonance absorption test made on the product shows a signal in 4.8 ppm which is considered due to the benzylation of the oxygen in the fifth position of pyrazole.

One gram of the resulting 1-(2,4,6-trichlorophenyl)-3-{2-chlor-5-[α-(2,4-di-t-amyl phenoxy)-butylamide]anilino}4-hydroxy-5-benzyloxy-pyrazole is dissolved in 20 ml of DMF, and then 0.2 g of KOH are added. 0.3 g of p-nitrophenyl chloroacetate are added to this, and the mixture is heated to 50° C. and reacted for two hours.

The reaction liquid is poured into iced water and extracted by use of 100 ml of ethyl acetate.

0.2 g of palladium charcoal (Pd/C) is added to the extracted liquid and the liquid is subjected to a catalytic reduction by hydrogen. The reaction is stopped when the liquid has absorbed a theoretical amount of hydrogen, and the product is subject to a post treatment and then refined by separation in the manner of a silica gel column chromatography.

The resulting principal product yield was 500 mg and the product had a melting point of 111°-112° C., while the yield of the byproduct was 100 mg, which resulted from the reduction of the nitro group of the principal product to an amino group.

1.7 g of benzyl chloride are added to the mixture at room temperature, which is then stirred over a period of 24 hours. 50 ml of water are subsequently added and heated to 40° C. for effecting the reaction for a period of two hours. The reaction liquid is poured into 350 ml of iced water, neutralized by the addition of acetic acid, and extracted by ethyl acetate. The solvent is removed by distillation under reduced pressure, and the resulting residuum is recrystallized by acetonitrile, thereby yielding 7 g (75%) of colorless needle crystals having a melting point of 185°-186° C.

Nuclear magnetic resonance absorption spectrum (CDCl$_3$); 2H singlet in 5.0 ppm.

Field Desorption Mass Spectrometry by electrolytic elimination: M+ 776.

EXAMPLE 4

Synthesis of 1-(2,4,6-trichlorophenyl)-3-{3-[α-2,4,-di-t-amyl phenoxy]acetamide]benzamide}-4-benzyloxy-5-pyrazolone.

Process (A): Substitution of blocking group.

10 g of 1-(2,4,6-trichlorophenyl)-3-{3-[α-(2,4,-di-t-amyl phenoxy)acetamide]benzamide}-4-benzoyloxy-5-pyrazolone (synthesized according to the method described in U.S. Pat. No. 3,311,476) are dissolved in 80 ml of acetone, and to the mixture are added 1.8 g of potassium carbonic anhydride and further are slowly added 2 g of methoxy methyl bromide with stirring at room temperature. Reaction occurs over a period of 8 hours.

The product of this reaction can also be obtained in low yield from the reaction of 1-(2,4,6-trichlorophenyl)-3-{3-[α-2,4,-di-t-amyl phenoxy acetamide]benzamide}-4-hydroxy-5-pyrazolone and methoxy methyl bromide.

The solvent is removed by distillation, and the resulting residuum is crystallized by ethyl acetate/n-hexane, thus yielding 9 g white powder crystals having a melting point of 145°-146° C. 9 g of the crystals are hydrolyzed by the addition of potassium hydroxide in alcohol to obtain 7.8 g of light yellow amorphous crystals.

Process (C): Etherification by two-equivalent substituent.

Process (D): Disassociation or removal of blocking group.

7.8 g of the resulting crystals are dissolved in 100 ml of dimethyl sulfoxide and to the mixture are added 2 g of NaOH and 2 g of benzyl chloride at room temperature. The reactants are stirred over a period of 24 hours. 500 ml of water are added to obtain crystals. These crystals are dissolved in 50 ml of acetic acid and to the mixture are added 0.5 ml of concentrated hydrochloride to be reacted at room temperature for 10 minutes. The resulting reaction liquid is poured into 500 ml of water and recrystallized by the addition of acetonitrile thereby to produce 7.5 g of colorless needle crystals having a melting point of 186°-187° C. The resulting product was confirmed to be identical with the coupler synthesized in Example 3 as a result of comparison test with an infrared spectrometer.

We claim:

1. A method for synthesizing a photographic magenta coupler having the general formula I:

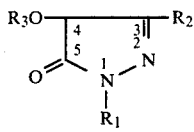

wherein $R_1$ is selected from the group consisting of an aryl group and a heterocyclic group, $R_2$ is selected from the group consisting of an acylamide group, an anilino group and a ureido group; and $R_3$ is selected from the group consisting of an alkyl group, a substituted alkyl group, an aryl group and a heterocyclic group, comprising the steps of:

(a) alkyl-, aryl- or heterocyclic etherifying a hydroxy group in the fourth position of a compound having the general formula II:

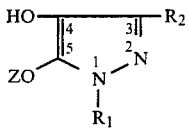

wherein $R_1$ and $R_2$ are as defined above and Z represents a blocking group selected from the group consisting of (1)

wherein X is oxygen or sulfur; and $R_4$ is selected from the group consisting of hydrogen, alkyl, aryl, heterocyclic, alkoxy, aryloxy, heterocyclic oxy, amino, alkylthio and heterocyclic thio; (2) —$SO_2R_5$, wherein $R_5$ is selected from the group consisting of alkyl, aryl, heterocyclic, hydroxy and amino; and (3) —$R_6$, wherein $R_6$ is selected from the group consisting of silyl, phosphoryl, benzyl, methoxymethyl, 2-pyranyl and phenacyl; and (b) removing said blocking group Z from said etherified compound to obtain said coupler having the general formula I.

2. A method for synthesizing a photographic magenta coupler having the general formula I:

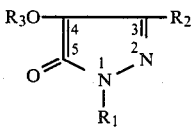

wherein $R_1$ is selected from the group consisting of an aryl group and a heterocyclic group, $R_2$ is selected from the group consisting of an acylamide group, an anilino group and a ureido group; and $R_3$ is selected from the group consisting of an alkyl group, a substituted alkyl group, an aryl group and a heterocyclic group, comprising the steps of:

(a) reacting a compound having the general formula

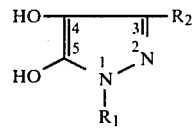

wherein $R_1$ and $R_2$ are as defined above, with a blocking agent to obtain a compound having the general formula II

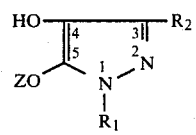

wherein $R_1$ and $R_2$ are as defined above and Z represents a blocking group selected from the group consisting of (1)

wherein X is oxygen or sulfur; and $R_4$ is selected from the group consisting of hydrogen, alkyl, aryl, heterocyclic, alkoxy, aryloxy, heterocyclic oxy, amino, alkylthio and heterocyclic thio; (2) —$SO_2R_5$, wherein $R_5$ is selected from the group consisting of alkyl, aryl, heterocyclic, hydroxy and amino; and (3) —$R_6$, wherein $R_6$ is selected from the group consisting of silyl, phosphoryl, benzyl, methoxymethyl, 2-pyranyl and phenacyl;

(b) reacting the compound having the general formula II with an etherification agent selected from the group consisting of an alkyl-etherification agent, an aryl-etherification agent and a heterocyclic-etherification agent to etherify the hydroxy group in the fourth position of said compound; and (c) removing said blocking group Z from the etherified compound having the general formula II to obtain said coupler having the general formula I.

3. The method of claim 1 wherein X is oxygen.

4. The method of claim 1 wherein $R_1$ is selected from the group consisting of phenyl, naphthyl, 2-chlorophenyl, 2,6-di-chlorophenyl, 2,4,6-trichlorophenyl, 3,5-dibromophenyl, 3-nitrophenyl, 4-(2,4-di-t-amyl phenoxy)acetamidophenyl, pentafluorophenyl, 4-phenoxyphenyl, 2,6-dimethyl-4-methoxyphenyl, 3-(N,N-diethyl sulfamyl)phenyl, 2,6-dichloro-4-methoxyphenyl, 2-dichloro-4,6-dimethyl phenyl, pentachlorophenyl, 2,6-dichloro-4-carboxyphenyl, 2,5-dimethoxy-3,4-dichlorophenyl, 4{α-(3-pentadecyl phenoxy)-butylamide}phenyl, 2-thiazolyl, 2-benzothiazolyl, 2-benzoxazolyl, 2-imidazolyl, and 2-benzoimidazolyl.

5. The method of claim 1 wherein $R_3$ is selected from the group consisting of ethoxycarbonyl ethyl, methoxyethyl aminocarbonyl propyl, phenyl methyl, n-butyl, hexyl, dodecyl, ethoxyethyl, 2-cyclopentanoneyl, methylsulfonyl butyl, tolyl sulfonyl methyl, 1-benzotriazolyl methyl, 2-benzothiazolyl ethyl, 3-carboxypropyl, perfluoropropyl, phenyl, 4-nitrophenyl, 3-cyanophenyl, 4-methyl sulfonyl phenyl, 4-hydroxyphenyl, 2-pyranyl, 2-pyridyl, 3-isoquinolyl, 1-phenyl tetrazolyl, 2-benzoxazolyl, triazolyl, and 3-indolyl.

6. The method of claim 4, whrerein $R_3$ is selected from the group consisting of ethoxycarbonyl ethyl, methoxyethyl aminocarbonyl propyl, phenyl methyl, n-butyl, hexyl, dodecyl, ethoxyethyl, 2-cyclopentanoneyl, methylsulfonyl butyl, tolyl sulfonyl methyl, 1-benzotriazolyl methyl, 2-benzothiazolyl ethyl, 3-carboxypropyl, perfluoropropyl, phenyl, 4-nitrophenyl, 3-cyanophenyl, 4-methyl sulfonyl phenyl, 4-hydroxyphenyl, 2-pyranyl, 2-pyridyl, 3-isoquinolyl, 1-phenyl tetrazolyl, 2-benzoxazolyl, triazolyl, and 3-indolyl.

* * * * *